(12) United States Patent
Cambron et al.

(10) Patent No.: US 8,178,045 B2
(45) Date of Patent: May 15, 2012

(54) INTERCHANGEABLE PRECONCENTRATOR CONNECTOR ASSEMBLY

(75) Inventors: Scott Cambron, Louisville, KY (US);
Thomas Roussel, Louisville, KY (US);
Robert Keynton, Louisville, KY (US);
Michael Martin, Louisville, KY (US);
Kevin Walsh, Louisville, KY (US);
Doug Jackson, New Albany, IN (US);
John Naber, Goshen, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 639 days.

(21) Appl. No.: 12/337,449

(22) Filed: Dec. 17, 2008

(65) Prior Publication Data

US 2009/0249958 A1 Oct. 8, 2009

Related U.S. Application Data

(60) Provisional application No. 61/007,873, filed on Dec. 17, 2007.

(51) Int. Cl.
*G01N 30/00* (2006.01)
*G01N 30/08* (2006.01)

(52) U.S. Cl. ............... 422/69; 422/70; 422/88; 422/89; 422/527; 422/560; 422/565; 73/23.41; 73/61.55; 96/104; 210/198.2

(58) Field of Classification Search ............ 422/69, 422/70, 88–89, 527, 554, 560, 565; 73/61.52–61.59, 73/23.35–23.42; 210/198.2; 96/101–107, 96/121
See application file for complete search history.

(56) References Cited

U.S. PATENT DOCUMENTS

| | | | | |
|---|---|---|---|---|
| 3,768,300 | A | * | 10/1973 | Nemeth ............... 73/23.26 |
| 4,011,301 | A | | 3/1977 | Young |
| 4,698,071 | A | | 10/1987 | Elias |
| 4,805,441 | A | | 2/1989 | Sides et al. |
| 4,839,143 | A | | 6/1989 | Vora et al. |
| 4,964,309 | A | | 10/1990 | Jenkins |
| 5,014,541 | A | | 5/1991 | Sides et al. |

(Continued)

FOREIGN PATENT DOCUMENTS

EP 00649337 B1 9/1996

(Continued)

OTHER PUBLICATIONS

Berger, T., et al., "Development of Electrochemical Sensors for Trace Detection of Explosives and for the Detection of Chemical Warfare Agents", Proceedings of the SPIE—The International Society for Optical Engineering, vol. 4038, pp. 452-461, 2000.

(Continued)

*Primary Examiner* — Jan Ludlow
(74) *Attorney, Agent, or Firm* — Stoll Keenon Ogden PLLC; Stephen C. Hall

(57) ABSTRACT

An interchangeable preconcentrator assembly comprises an outer housing and an inner housing defining a chamber. A biased urging member is held at least partially within the outer housing and slidably biased toward a surface of the inner housing. When the biased urging member is at least partially retracted, a space is defined between the urging member and the surface of the inner housing for accommodating at least one preconcentrator chip. A continuous fluid flow path is defined through the outer housing and through the space. The interchangeable preconcentrator assembly may further comprise at least one modular preconcentrator carriage.

19 Claims, 6 Drawing Sheets

U.S. PATENT DOCUMENTS

| | | | |
|---|---|---|---|
| 5,035,776 A | 7/1991 | Knapp et al. | |
| 5,053,343 A | 10/1991 | Vora et al. | |
| 5,083,019 A | 1/1992 | Spangler | |
| 5,092,155 A | 3/1992 | Rounbehler et al. | |
| 5,092,218 A | 3/1992 | Fine et al. | |
| 5,142,143 A | 8/1992 | Fite et al. | |
| 5,395,589 A | 3/1995 | Nacson | |
| 5,578,271 A | 11/1996 | Simon et al. | |
| 5,707,502 A | 1/1998 | McCaffrey et al. | |
| 5,753,832 A | 5/1998 | Bromberg et al. | |
| 5,792,423 A | 8/1998 | Markelov | |
| 5,817,012 A | 10/1998 | Schoendorfer | |
| 5,847,291 A | 12/1998 | Green et al. | |
| 5,854,431 A | 12/1998 | Linker | |
| 5,932,482 A | 8/1999 | Markelov | |
| 5,970,803 A | 10/1999 | Staples et al. | |
| 6,001,308 A | 12/1999 | Marlow et al. | |
| 6,022,748 A | 2/2000 | Charych et al. | |
| 6,057,162 A | 5/2000 | Rounbehler et al. | |
| 6,066,295 A | 5/2000 | Bernstein et al. | |
| 6,085,601 A | 7/2000 | Linker | |
| 6,087,183 A | 7/2000 | Zaromb | |
| 6,171,378 B1 | 1/2001 | Manginell et al. | |
| 6,239,428 B1 | 5/2001 | Kunz | |
| 6,242,195 B1 | 6/2001 | Idusogie et al. | |
| 6,257,835 B1 | 7/2001 | Kaehler | |
| 6,295,860 B1 | 10/2001 | Sakairi et al. | |
| 6,316,268 B1 | 11/2001 | Yang | |
| 6,326,615 B1 | 12/2001 | Syage et al. | |
| 6,345,545 B1 | 2/2002 | Linker et al. | |
| 6,354,160 B1 | 3/2002 | Staples et al. | |
| 6,442,997 B1 | 9/2002 | Megerle | |
| 6,485,987 B1 | 11/2002 | Charych et al. | |
| 6,527,835 B1 | 3/2003 | Manginell et al. | |
| 6,619,143 B2 | 9/2003 | Danylewych-May et al. | |
| 6,666,907 B1 | 12/2003 | Manginell et al. | |
| 6,706,091 B1 | 3/2004 | Robinson et al. | |
| 6,811,587 B1 | 11/2004 | Lorey | |
| 6,869,501 B2 | 3/2005 | Davidson et al. | |
| 6,893,879 B2 | 5/2005 | Petersen et al. | |
| 6,914,220 B2 | 7/2005 | Tian et al. | |
| RE38,797 E | 9/2005 | Linker | |
| 6,989,891 B2 | 1/2006 | Braig | |
| 7,104,112 B2 | 9/2006 | Bonne | |
| 7,141,786 B2 | 11/2006 | McGann et al. | |
| 7,244,288 B2 | 7/2007 | Belyakov | |
| 7,273,517 B1 | 9/2007 | Lewis et al. | |
| 7,306,649 B2 | 12/2007 | Boyle | |
| 2002/0055184 A1 | 5/2002 | Naylor et al. | |
| 2003/0084789 A1* | 5/2003 | Kim | 96/121 |
| 2004/0035226 A1 | 2/2004 | Allen et al. | |
| 2004/0035227 A1 | 2/2004 | Allen et al. | |
| 2004/0060346 A1 | 4/2004 | Bonne et al. | |
| 2005/0014134 A1 | 1/2005 | West | |
| 2005/0095722 A1 | 5/2005 | McGill et al. | |
| 2005/0226778 A1 | 10/2005 | Houser et al. | |
| 2005/0253061 A1 | 11/2005 | Cameron et al. | |
| 2006/0257287 A1 | 11/2006 | Call | |
| 2006/0288872 A1* | 12/2006 | Nakano | 96/108 |
| 2007/0084347 A1 | 4/2007 | Boyle et al. | |
| 2007/0176092 A1 | 8/2007 | Miller et al. | |
| 2009/0028208 A1 | 1/2009 | Martin | |
| 2009/0090197 A1 | 4/2009 | Finlay | |

FOREIGN PATENT DOCUMENTS

| | | |
|---|---|---|
| EP | 0502998 B1 | 7/1999 |
| GB | 02243917 A | 11/1991 |
| WO | WO 97/35174 A1 | 9/1997 |
| WO | WO 2004052540 A2 | 6/2004 |
| WO | WO 2004083806 A2 | 9/2004 |
| WO | WO 2005029030 A2 | 3/2005 |
| WO | WO 2006013396 A2 | 2/2006 |
| WO | WO 2006046077 A1 | 5/2006 |
| WO | WO 2006046988 A1 | 5/2006 |
| WO | WO 2006073434 A2 | 7/2006 |
| WO | WO 2006073440 A2 | 7/2006 |
| WO | WO 2006104603 A2 | 10/2006 |
| WO | WO 2007041551 A2 | 4/2007 |
| WO | WO 2007044473 A2 | 4/2007 |
| WO | WO 2007056488 A1 | 5/2007 |

OTHER PUBLICATIONS

Cabalo, J., et al., "Trace Detection of Explosives with Low Vapor Emissions by Laser Surface Photofragmentation-Fragment Detection Spectroscopy with an Improved Ionization Probe", Applied Optics, vol. 44, No. 6, pp. 1084-1091, Feb. 20, 2005.

Da Silva, J. A. F., et al., Simulations of silicon microstructure for preconcentration of metallic ions, Microelectronics Technology and Devices. SBMICRO 2003. Proceedings of the Eighteenth International Symposium, Sep. 2003, pp. 420-427, Pennington, NJ, USA.

Davidson, William R., et al., "Vapor and Particle Sampling in the Detection of Terrorists Explosives", Proc. 50$^{th}$ ASMS Conf. Mass Spectrom. Allied Top., pp. 697-698, 2002.

Ewing, R. G., et al., "Detection of Volatile Vapours Emitted from Explosives with a Handheld Ion-Mobility Spectrometer", Field Analytical Chemistry and Technology, vol. 5, No. 5, pp. 215-221, 2001.

Fisher, M., et al., "Explosive Detection Using High-Volume Vapor Sampling and Analysis by Trained Canines and Ultra-Trace Detection Equipment", Proceedings of the SPIE—The International Society for Optical Engineering, vol. 5403, No. 1, pp. 409-417, Apr. 12-16, 2004.

Goeringer, Douglas, et al., "Comparison of Atmospheric Pressure Chemical Ionization and Atmospheric Sampling Glow Discharge Ionization Combined with Tandem Mass Spectrometry for Explosives Vapor Detection", Proc. 50$^{th}$ ASMS Conf. Mass Spectrom. Allied Top., pp. 707-708, 2002.

Hannum, David W., et al., "Miniaturized Explosive Preconcentrator for Use in a Man-Portable Field Detection System", International Nuclear Materials Management Conference, Phoenix, AZ, Aug. 2, 1999.

Ho, C.K., et al., "Integrated Chemiresistor Sensors with Preconcentrators for Monitoring Volatile Organic Compounds in Water", Proceedings of the 2005 World Water and Environmental Resources Congress. EWRI 2005: Impacts of Global Climate Change, Anchorage, Alaska, May 15, 2005.

Holland, R.M., et al., "Handheld GC instrumentation for Chemical Weapons Convention treaty verification inspections MONOGRAPH TITLE—Field screening methods for hazardous wastes and toxic chemicals. VIP-47, vol. 1", Air and Waste Management Association, Pittsburgh, PA, 1995.

Hughes, David, "Explosive Detection Equipment Firms Develop Enhanced X-Ray and Vapor Technologies", Aviation Week & Space Technology, vol. 134, No. 12, pp. 60-62, Mar. 25, 1991.

Hughes, R. C., et al., "Chemical sensing with an integrated preconcentrator/chemiresistor array", Chemical and Biological Sensors and Analytical Methods II Proceedings of the International Sympsoium, 2001, pp. 348-354, Electrochemical Society, Pennington, NJ, USA.

Lucero, Daniel P., "User Requirements and Performance Specifications for Explosive Vapor Detection Systems", Journal of Testing & Evaluation, vol. 13, No. 3, pp. 222-233, 1985.

Martin, Michael, et al., "Microfabricated vapor preconcentrator for portable ion mobility spectroscopy", Sensors and Actuators, B: Chemical, vol. 126, No. 2, Oct. 1, 2007.

McGill, R. A., et al., "A micromachined preconcentrator for enhanced trace detection of illicit materials, 2003 International Semiconductor Device Research Symposium", IEEE, Piscataway, NJ, USA.

Owano, T. G., et al., "Ultrasensitive Detection of Explosives Vapor Using Mid-IR Cavity Ring-Down Spectroscopy", Technical Digest. Summaries of papers presented at the Conference on Lasers and Electro-Optics, Postconference Technical Digest, pp. 519-520, 2001.

Ritchie, Robert K., et al., "Detection of Explosives, Narcotics, and Taggant Vapors by an Ion Mobility Spectrometry Particle Detector", Proceedings of the SPIE—The International Society for Optical Engineering, vol. 2092, pp. 87-93, 1994.

Parmeter, J.E., et al., "Development of a portable preconcentrator/ion mobility spectrometer system for the trace detection of narcotics", Sandia National Labs. Report, Albuquerque, NM, Aug. 1997.

Parmeter, J.E., et al., "Explosives detection portal for high-volume personnel screening", Proceedings of the 1998 Enforcement and Security Technologies, Boston, MA, 1999.

Parmeter, John, et al., "Overview of Explosives Detection Research and Development in Department 5848 at Sandia National Laboratories", 16th Annual NDIA Security Technology Symposium & Exhibition, Jun. 26-29, 2000.

Rodacy, Philip J., et al., "Unexploded ordnance classification sensor for underwater applications", Sandia National Labs. Report, Albuquerque, NM, Apr. 1, 2000.

Rhykerd, C., et al., "Airport testing an explosives detection portal", Institute of Nuclear Materials Management (INMM) annual meeting, Naples, FL, Jul. 26-30, 1998.

Seman, G., et al., "Detection of Hidden Explosives on Passenger Aircraft Using Hand Searches, Bio-Sensors and Vapour Detectors", Proceedings of the 1977 International Conference on Crime Countermeasures—Science and Engineering, pp. 65-84, 1977.

Sigman, M. E., et al., "Performance Evaluation of an In-Injection Port Thermal Desorption/Gas-Chromatographic/Negative Ion Chemical Ionization Mass Spectrometric Method for Trace Explosive Vapour Analysis", Analytical Chemistry, vol. 73, No. 4, pp. 792-798, Feb. 15, 2001.

Simoes, E.W., et al., "Study of preconcentration of non-polar compounds in microchannels with constrictions", Sensors and Actuators, vol. 115, No. 1, Lausanne, Switzerland, May 23, 2006, pp. 232-239.

Spicer, James B., et al., "Overview: MURI Center on Spectroscopic and Time Domain Detection of Trace Explosives in Condensed and Vapor Phases", Proc. SPIE Int Soc Opt Eng., vol. 5089, No. 2, pp. 1088-1094, 2003.

Staples, Edward J., et al., "Ultrahigh-Speed Chromatography and Virtual Chemical Sensors for Detecting Explosive and Chemical Warfare Agents", IEEE Sensors J., vol. 5, No. 4, pp. 622-631, Aug. 2005.

Voiculescu, I., et al., "Micropreconcentrator for Enhanced Trace Detection of Explosives and Chemical Agents", IEEEE Sensors Journal, vol. 6, No. 5, pp. 1094-1104, Oct. 2006.

"Smiths Detection Introduces Next-Generation Handheld Detector for Narcotics, Explosives, Chemical Warfare Agents and Toxic Industrial Chemicals", Smiths Detection, Pine Brook, NJ, Jun. 3, 2004.

"Technest Provides Status Update on Remote Standoff Chemical Agent and Explosives Detection Sensor Development Program", Technest Holdings Inc., Boston, MA, Jan. 16, 2006.

U.S. Appl. No. 11/881,333, filed Jul. 25, 2007, Martin.
U.S. Appl. No. 11/542,453, filed Oct. 2, 2006, McGill et al.
U.S. Appl. No. 10/865,685, filed Jun. 10, 2004, McGill et al.
U.S. Appl. No. 12/406,756, filed Mar. 18, 2009, Martin et al.

Hughes, R.C., et al., "A Mems Based Hybrid Preconcentrator/Chemiresistor Chemical Sensors", Sandia National Laboratories, Albuquerque, N.M., MS 1425, 87185.

McGill, R. A., et al., "Choosing Polymer Coatings for Chemical Sensors", ChemTech, Sep. 1994, pp. 27-37.

Parmeter, J.E., et al., "Overview of Explosives Detection Research and Development in Department 5848 at Sandia National Laboratories", Sandia National Laboratories, Albuquerque, N.M., MS 0782, 87185.

Sandia National Laboratories Fact Sheet, "Micro Analytical Systems Department Technology—μChemLab™".

* cited by examiner

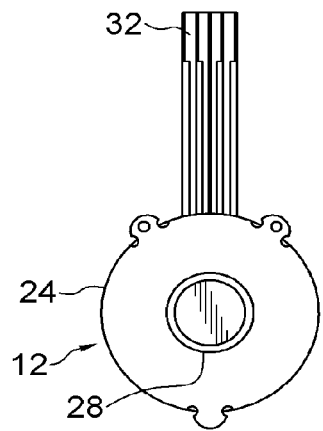 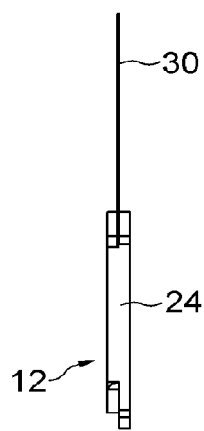 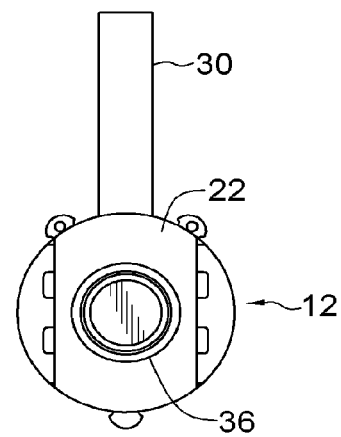
FIG. 3A  FIG. 3B  FIG. 3C
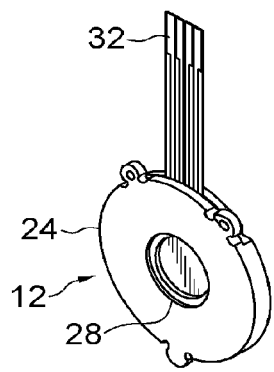 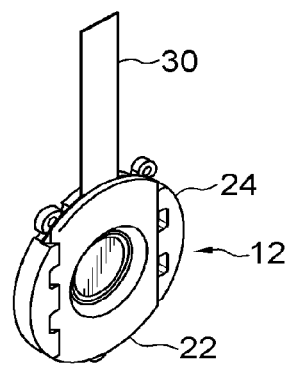
FIG. 3D  FIG. 3E

INTERCHANGEABLE PRECONCENTRATOR CONNECTOR ASSEMBLY

PRIORITY CLAIM AND REFERENCE TO RELATED APPLICATION

This application claims the benefit of U.S. Provisional Application Ser. No. 61/007,873, filed Dec. 17, 2007, under 35 U.S.C. §119, which is incorporated by reference herein.

STATEMENT OF GOVERNMENT INTEREST

This invention was made with Government support under DoJ-NIJ #2004-IJ-CXK055. The Government has certain rights in the invention.

FIELD OF THE INVENTION

A field of the invention is analyte collection. The invention may be useful, for example, in analyte detection and analysis systems and methods, as might be used for the collection, detection, and analysis of a wide range of vapors or gases, particulate, and liquid-bound analytes.

BACKGROUND OF THE INVENTION

Analyte detection is becoming increasingly important as a security and safety measure. Transportation, commercial, government, educational, and other facilities have a need for the sensitive and rapid detection of analytes, such as those that are indicative of explosives or other substances that pose a threat. In addition, in industrial, residential, and commercial settings, analyte detection can provide warning of particles that pose a health or safety risk. Example analytes to be detected include, for example, hazardous materials, including explosive-related materials, toxic industrial chemicals (TICS), narcotics, or chemical or biological agents.

Analysis instruments have been developed and are under development to meet the needs for detection of analytes. A nonlimiting example analysis instrument that is currently used in portable and larger forms is the Ion Mobility Spectrometer (IMS), such as the GE VaporTrace models. Speed and sensitivity are primary concerns in any such instruments. Researchers and manufacturers seek to improve the sensitivity of such analysis instruments.

A typical IMS device has separate particle and vapor modes. In particle mode, an assembly is affixed to the device to accept and desorb particles from a substrate such as a swab, for example, during baggage screening. The swab is inserted into the assembly, is heated to desorb any collected particulates, and the particulates are directed via vacuum into the instrument for analysis. Another assembly can be affixed to the device for vapor mode, in which the device collects vapors for analyte detection. This mode, for example, is commonly used to sample contained areas such as automobile trunks at the entrances to military facilities.

Preconcentrators offer the opportunity to enhance the performance of any type of analysis instrument by increasing the concentration of analyte in a volume of fluid sent for analysis. Generally, preconcentrators collect analyte over a period of time (during absorption) and then provide a concentrated fluid stream to the analysis device (during desorption). Desorption requires rapid heating, and microscale preconcentrators accordingly have advantages regarding thermal cycling and desorption, since heating for accomplishing desorption can be conducted quickly and with low power.

Microscale preconcentrators are disclosed in Manginell et al., U.S. Pat. No. 6,527,835, entitled Chemical Preconcentrator with Integral Thermal Flow Sensor, and in Manginell et al., U.S. Pat. No. 6,171,378, entitled Chemical Preconcentrator. The chemical preconcentrator used in that work is formed from a substrate having a suspended membrane, such as low-stress silicon nitride. This work incorporates a flow over design.

Successful microscale preconcentrators with a flow-through design are disclosed in U.S. Patent Application Publication No. 20050095722 (incorporated by reference herein), published May 5, 2005, and entitled "Microscale Flow Through Sorbent Plate Collection Device", and in U.S. Patent Application Publication No. 20050226778, published Oct. 13, 2005, and entitled "Microscale Flow Through Sorbent Plate Collection Device". The flow through design has a number of advantages, one of which is increasing contact between the analyte fluid flow and the sorbent in the collection area compared to typical flow over designs that would require creating a turbulent flow to match the level of analyte fluid-sorbent contact.

Lacking in the art is a practical and reliable interface that can easily and efficiently integrate a microscale preconcentrator with analysis instruments. A macroscale assembly for a large screen style preconcentrator has been developed and published by researchers at Sandia National Laboratories. See "Overview of Explosives Detection Research and in Development", 16$^{th}$ Annual NDIA Security Technology Symposium & Exhibition, Jun. 26-29, 2000 John E. Parmeter, David W. Hannun, Kevin L. Linker, and Charles L. Rhykerd. This technology includes a large screen (a few inches in diameter) that accepts fluid (e.g., air) flow through a large round opening, and concentrated explosive molecules/ partners via adsorption on the pleated screen. A custom block assembly attaches the preconcentrator to an IMS device.

SUMMARY OF THE INVENTION

According to example embodiments of the present invention, an interchangeable preconcentrator assembly is provided. An example interchangeable preconcentrator assembly comprises an outer housing and an inner housing defining a chamber. A biased urging member is held at least partially within the outer housing and slidably biased toward a surface of the inner housing. When the biased urging member is at least partially retracted, a space is defined between the urging member and the surface of the inner housing for accommodating at least one preconcentrator chip. A continuous fluid flow path is defined through the outer housing and through the space.

The interchangeable preconcentrator assembly may further comprise at least one modular preconcentrator carriage. An example modular preconcentrator carriage comprises a microscale preconcentrator chip including a plurality of throughholes and a heater for heating a surface of the chip, and first and second plates at least partially enclosing the chip. At least one electrode is coupled to the heater and extends beyond the first and second plates.

BRIEF DESCRIPTION OF THE DRAWINGS

FIG. 1A is a top plan view, FIG. 1B is a front elevation view, FIG. 1C is a side elevation view, FIG. 1D is a rear perspective view, and FIG. 1E is a front perspective view;

FIGS. 3A-3E show various views of the example preconcentrator disk carriage package of FIG. 2, where FIG. 3A is a rear elevation view, FIG. 3B is a side elevation view, FIG. 3C is a front elevation view, FIG. 3D is a rear perspective view, and FIG. 3E is a front perspective view;

DETAILED DESCRIPTION

Figure 1A:
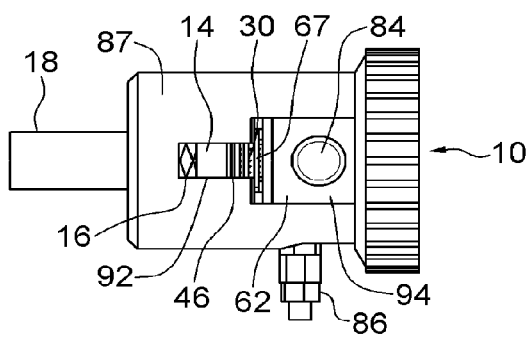
FIGS. 1A-1E show an example interchangeable preconcentrator assembly according to an embodiment of the present invention, where
Figure 1B:
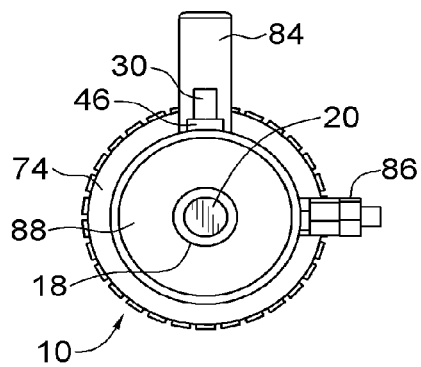
Figure 1C:
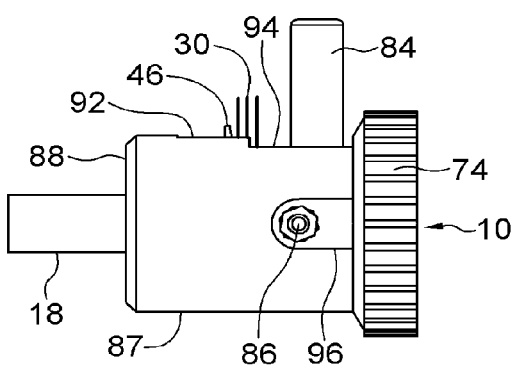
Figure 1D:
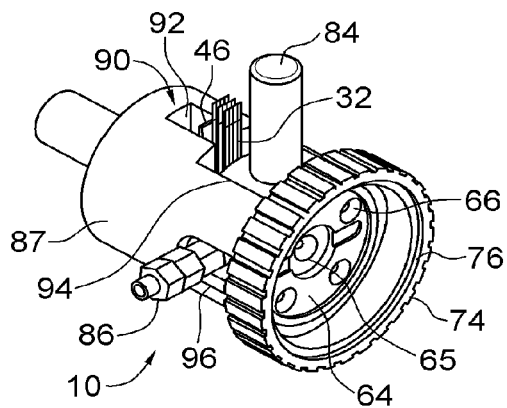
Figure 1E:
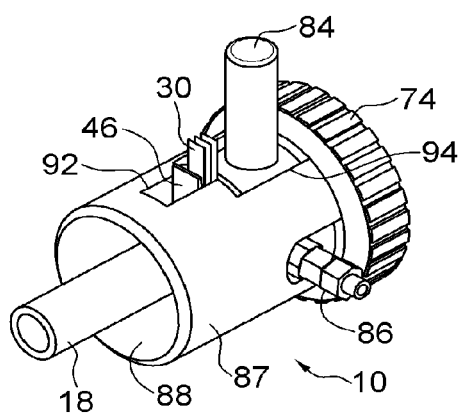
Figure 2:
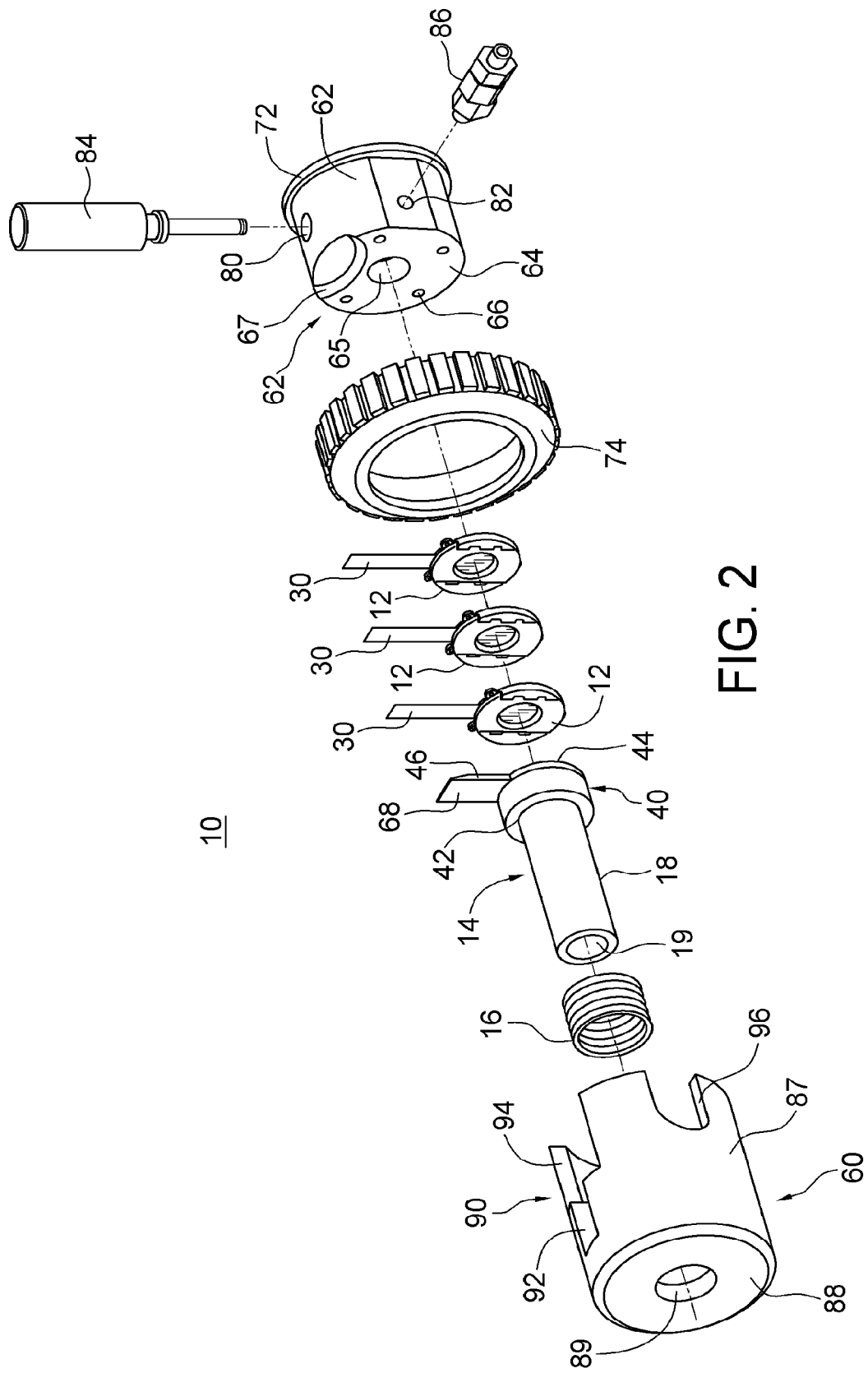
FIG. 2 is an exploded perspective view of the interchangeable preconcentrator assembly of FIGS. 1A-1E.
Figure 4:
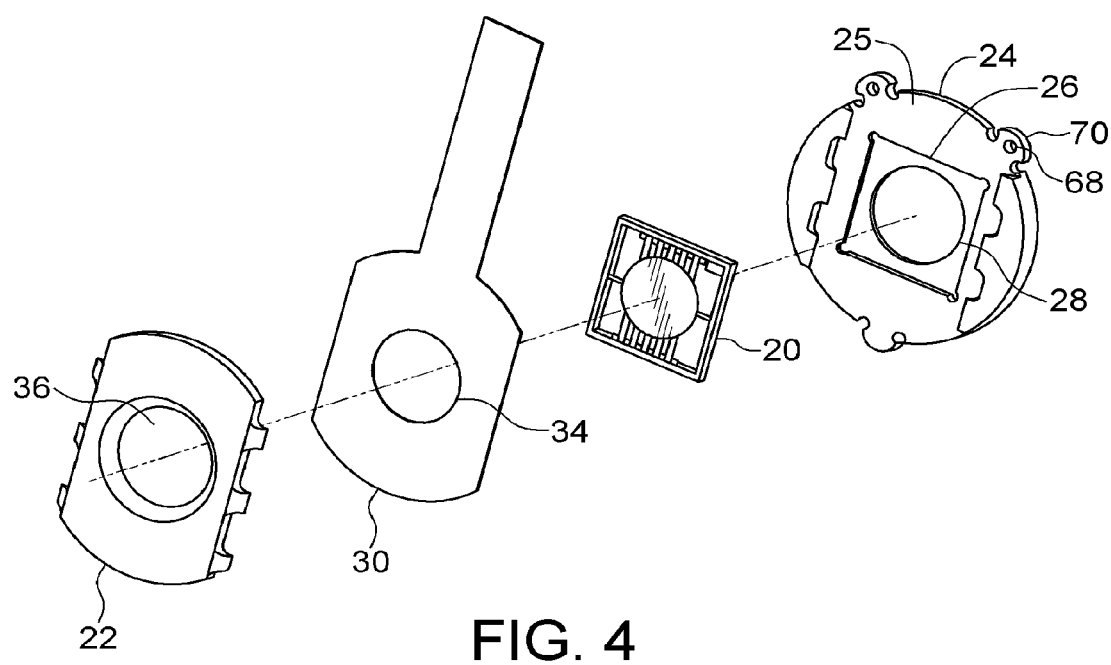
FIG. 4 shows an exploded view of the example preconcentrator disk of FIGS. 2 and 3A-3E.

Example embodiments of the invention provide, among other things, an interchangeable preconcentrator connector assembly that permits rapid sequential insertion and removal of packaged analytical microscale preconcentrators into a stacked formation to focus or preconcentrate a desired sample of vapors and/or particles prior to desorption into a storage or analysis instrument. The analytical preconcentrators are microscale preconcentrators held in a protective carriage that includes electrodes for connection to a control circuit. A biased member in the assembly pushes against one or more inserted preconcentrator(s) held within a space provided within an outer housing to align and secure them such that fluid flow will be primarily through the preconcentrators from an inlet to the assembly. Valves in the assembly allow flows for preconcentration that are independent from flows of analysis instrument.

An example assembly of the invention can be configured to attach to different analysis instruments. A nonlimiting example application of an assembly of the invention is for attaching to an ion mobility spectrometer (IMS). Thus, a nonlimiting example embodiment of the invention is configured to attach to an IMS or be formed as part of the IMS. An example assembly accepts a number (as an example, up to 5, though this number can be lower or higher) carriages containing microscale preconcentrators. An urging member and biasing member arrangement in a preferred embodiment is biased against the cartridges to accept them, hold them, and permit removal, while also limiting flow to be primarily through the preconcentrators. With the example stacked arrangement, a significant increase in sample signal sensitivity can potentially be achieved, and the assembly permits the interchanging, replacement, and rearranging of packaged preconcentrators. The example assembly accepts one or more carriages containing preconcentrators as modules, permitting readily the addition and/or removal of preconcentrator chips to reach desired sensitivity levels, and/or to concentrate or exclude particular analytes. The nature of testing to be conducted can be changed on the fly with a simple change of preconcentrator chip(s).

Preferred embodiments will now be discussed with respect to the drawings. The drawings include schematic figures that are not to scale, which will be fully understood by skilled artisans with reference to the accompanying description. Features may be exaggerated for purposes of illustration. From the preferred embodiments, artisans will recognize additional features and broader aspects of the invention. While example embodiments will be described as configured for an IMS, an assembly of the invention could also be configured to attach, for example, to any suitable analyzer, such as but not limited to a gas chromatography column or other analytical instrument. The example connector assembly is configured to attach to or be an integral part of a storage or analysis instrument.

An example embodiment interchangeable preconcentrator assembly 10 of the invention is shown in FIGS. 1A-1E, and FIG. 2 shows an exploded view of the assembly. Within the assembly 10, at least one disk-shaped preconcentrator carriage 12, and preferably a plurality of carriages, are accepted under bias supplied by an urging member such as but not limited to a plunger 14, which in turn is biased by a biasing member, such as but not limited to a spring 16. The plunger 14 and the spring 16 together provide biasing via spring loading for maintaining position of the preconcentrator carriages 12. A tube portion 18 of the plunger includes an opening 19 completely there through to provide an inlet for a continuous fluid flow path through the assembly 10, including through the microscale preconcentrator carriages 12. However, it is also contemplated that the fluid flow path may be around or adjacent to the urging member in other embodiments, and in this case a substantially hollow tube portion 18 may not be necessary. Preferably, the plunger 14 is comprised of a material with high thermal capacity and conductivity, and maintains constant bias on the installed stacked preconcentrators 12 via a spring such as spring 16.

FIGS. 3A-3E and 4 show additional features of the example interchangeable preconcentrator carriages 12. Each example preconcentrator carriage 12 includes a microscale preconcentrator chip 20 that is held within opposed front and back outer plates 22, 24. The front and back outer plates 22, 24, in an example embodiment, engage one another at an outer seat 25 of the outer plate via a snap fit to generally enclose the carriage and protect the preconcentrator chip. Preferably, except for the outer seat 25, the back outer plate 24 is disk (e.g., circular or oval) shaped, and the outer seat 25 (and thus the front outer plate) is generally oval or round in shape, except for the locking members (e.g., flexures) used for the snap fit. The front and back outer plates 22, 24 are preferably made of a low thermal conductive material, such as but not limited to Polyetheretherketone (PEEK) material. To secure the preconcentrator chip 20, an inner seat 26 shaped to match (or at least constrain movement of) the preconcentrator chip is provided on the back outer plate 24. The seat 26 includes an opening 28 (as shown by example in FIGS. 1-4, a circular opening) aligned with at least a portion of a surface of the preconcentrator chip 20 for allowing fluid flow to and from the preconcentrator chip. Example features of individual microscale preconcentrator chips are provided in U.S. Patent Application Publication No. 20050095722 (incorporated by reference herein), published May 5, 2005, and entitled "Microscale Flow Through Sorbent Plate Collection Device", though any suitable flow-through microscale preconcentration chip, preferably with a selectively activated heater, may be used.

A flex circuit 30, e.g., a polyimide thin film flex board, used for external device powering is inserted between the front outer plate 22 and the microscale preconcentrator chip 20, and is bonded to the preconcentrator chip prior to final assembly of the carriage 12 to enable connection to integral resistive heater traces on the microscale preconcentrator chips. The example flex circuit 30 includes (e.g., printed thereon) one or more electrical connections to resistive heaters included in the microscale preconcentrator chip. Contact electrodes 32, for example, formed on the flex circuit 30 (e.g., printed on a rear side of the flex circuit), extend beyond the front and back outer plates 22, 24, and thus are exposed so that the heating for the adsorption and desorption cycles of the preconcentrators can be selectively controlled. Similarly, the flow can be controlled via valves independently from an analysis instrument to which the assembly 10 is electrically connected. An opening 34, preferably aligned with the opening 28, is provided in the flex circuit 30 to allow fluid flow therethrough. The front outer plate 22 also includes an opening 36 aligned with the openings 28, 34 for allowing fluid flow.

In an example embodiment, the plunger 14 includes a head 40 at one end of the tube 18. The head 40, which may be formed integrally with or coupled to the tube 18, includes a front surface 42 for contacting and longitudinally constraining the spring 16, and an engaging surface 44 for engaging the front plate 22 of one of the preconcentrator carriages 12. An extension 46 is preferably provided either as an integral part of or a separate part connected to the head 40 for supporting the contact electrodes 32 when the assembly 10 is completed. The extension 46 also provides a handle to move the plunger 14 within the assembly 10.

To enclose the assembly 10 and provide an inner chamber for the preconcentrator carriages 12, a generally cylindrical outer housing 60 and a generally cylindrical inner housing 62 are provided. The inner housing 62, preferably provided at the rear of the assembly 10, includes a plate 64 having a generally circular surface for engaging a surface of the back plate 22 of one of the carriages 12. This surface includes a throughhole 65 providing a continuous fluid flow path. In this way, when the plunger 14 is at least partially retracted (e.g., moved towards the front of the assembly 10, against the bias of the spring 16), a space is defined between the plunger (for example, the surface 44 of the plunger) and the surface of the plate 64 for accommodating the preconcentrator carriages 12. Due to the opening 19 in the tube 18, the fluid flow is continuous through the plunger 14, through this space (and thus through any preconcentrator chips 20 within the space), and through the throughhole 65 in the inner surface 62. Throughholes 66 formed in the plate 64 allow for fasteners to attach the plate 64 to the outer housing 60. Additionally, the plate 64 includes a lead-in 67 (e.g., a chamfer) machined in the inner housing for accepting the carriages 12 as they are inserted into the assembly 10. A wedge 68 is provided at an end of the extension 46 to also provide a lead-in. The lead-in 67 and/or the wedge 68 in the example embodiment allow the carriages 12 to be inserted into the assembly and accordingly retract the plunger 14, without first needing to separately retract the plunger.

A circular flange 72 is provided on the outside of the inner housing 62 to engage an inner surface of a threaded ring 74, which is placed around the outer surface of the outer housing 60. The threaded ring 74 includes threads 76 for connecting the assembly 10 to an inlet of an analysis device. To provide independent valve operation of the assembly 10, the inner housing 62 may include one or more openings 80, 82 for receiving one or more valves 84, 86.

The inner housing 62 is preferably formed of a material with high thermal capacity and conductivity, such that the assembly 10 can be used as a heat source for scavenging heat from the analysis instrument to which it is connected. This scavenged heat can be used to keep the assembly 10 at an elevated temperature to prevent any sample vapors and/or particles from attaching to exposed internal flow surfaces during collection/detection.

The outer housing 60 surrounds the inner housing 62 and provides a generally cylindrical outer surface 87 for the assembly 10. The outer housing 60 is preferably formed from a low thermal conductivity material, such as PEEK, to act as a thermal insulation layer, to minimize out-gassing, and to enclose the entire stacked preconcentrator assembly 10 with an adequate seal that prevents the sample fluid/air from escaping. A front plate 88 of the outer housing 60 includes an opening 89 for slidingly engaging the tube portion 18 of the plunger 14, so that when assembled, the tube portion 18 extends through the opening (best shown in FIGS. 1A-1E). When assembled in this way, the spring 16 is seated in a cylinder formed between the head 40 of the plunger 14 and the bottom of the outer housing 60 carriage sleeve. For accommodating the flex electrodes 30, the extension 46, and the valve 84 (if used), the outer housing 60 includes a generally T-shaped slot 90 along the cylindrical outer surface 87. The slot 90 has a longitudinally extending part 92 for accepting the extension 46, and permits longitudinal movement of the flex electrodes 30 and the extension within the T-shaped slot, while maintaining alignment of the plunger 14 within the assembly 10. A laterally wider part 94 of the T-shaped slot 90 surrounds one or more of the flex electrodes 30 (one or more of which may instead be surrounded by the longitudinally extending part 92 if the plunger 14 is moved forward to a large extent), and accommodates the valve 84 extending from the inner housing 62. To accommodate the other valve 86, another longitudinally extending slot 96 may be provided.

To construct the assembly 10, one or more of the preconcentrator carriages 12 may be prepared by, for example, bonding the flex circuit 30 to the preconcentrator chip 20, placing the flex circuit and the microscale preconcentrator chip 20 on the outer seat 25 of the back outer plate 24 (such that the preconcentrator chip is placed into the inner seat 26), and snap fitting the front outer plate 22 into the inner seat of the back outer plate. These preconcentrator carriages 12 may be selected, configured, and/or assembled when constructing the overall assembly 10, or at any prior time. Further, the preconcentrator carriages 12 may be assembled at a different location than the overall assembly 10 and then selected for use.

The rest of the assembly 10 may be constructed by inserting the tube portion 18 of the plunger 14 through the spring 16 and then through the opening 89 of the outer housing 60. The threaded ring 74 is placed around the inner housing 62, and the inner housing is inserted into the outer housing 60. The valves 84, 86 are inserted into the inner housing 62 via the openings 80, 82. The throughhole 66 formed in the plate 64 allow fasteners to attach the plate 64 to the outer housing 60.

The assembly 10 can incorporate seals at points as a further limitation of flows to direct flow during collection primarily through the microscale preconcentrator chips 20 and the appropriate valves 84, 86. Nonlimiting example points include between carriages 12, between the plunger 14 and the carriages, etc.

To load the assembled spring loaded housing assembly 10, the packaged preconcentrator microscale carriages 12 are sequentially dispensed into the assembly, for example, using a pair of tweezers/forceps, by sliding the packaged preconcentrator microscale carriages 12 between the plunger lead in plate 68 of the extension 46 (loaded by the spring 16) and the surface of the lead-in 67 that is machined into the inner housing 62. The configuration of the carriages, 12, including the general disk shape, the outer surface of the outer plate 24, and the flex circuit 30, in combination with the longitudinal slot of the outer housing, permits sliding movement of the carriages 12 within the outer housing, while maintaining alignment of the carriages. Further, the example configuration of the outer housing, and more particularly the longitudinal slot, combined with the extension of the plunger 14, allows similar sliding movement of the plunger within the outer housing. Releasing the plunger 14 slidingly urges the plunger against the preconcentrator microscale carriages 12 to hold them in place, aligned with the fluid flow path created by the opening 89 of the outer housing 60, tube opening 19, and opening 65 of the inner housing 62.

Figure 5A:
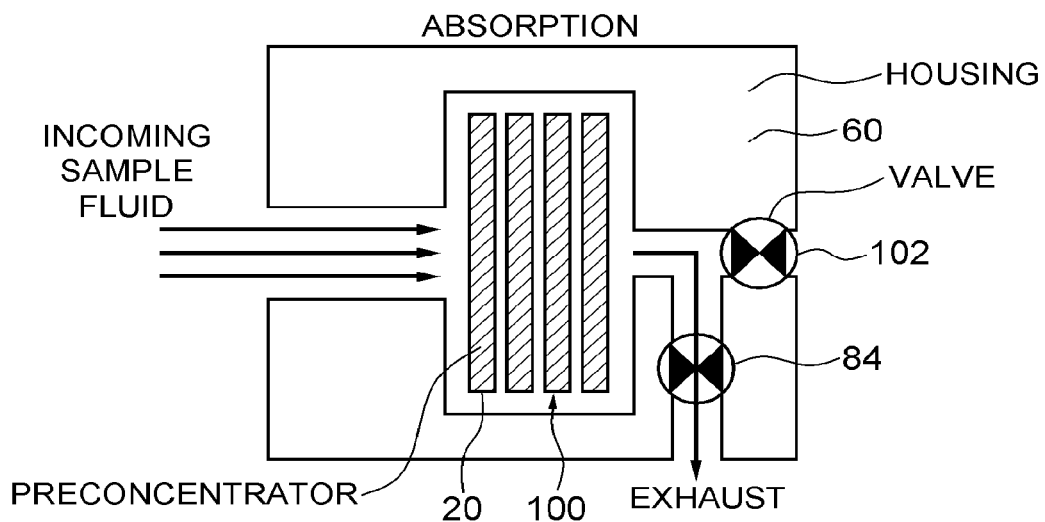
FIGS. 5A-5B are schematic cross-section views illustrating adsorption and desorption flows, respectively, for the assembly shown in FIGS. 1-4.
Figure 5B:
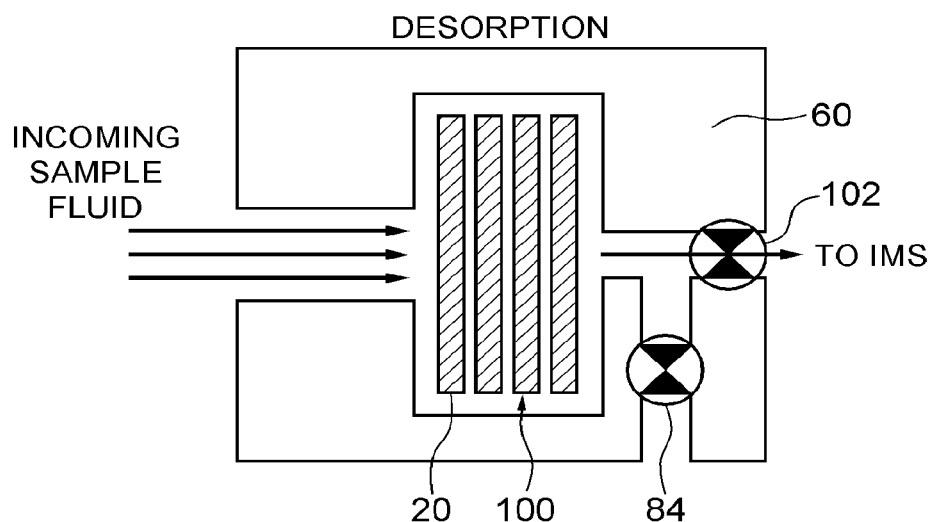

Referring now to FIGS. 5A and 5B, shown are schematic cross-section views illustrating adsorption and desorption flows of the example assembly 10 of FIGS. 1-4. In the absorption mode, shown in FIG. 5A, sample fluid/air passes through a stack 100 of unheated analytical preconcentrators 20, collecting desired vapors and/or particles. At this time, a valve 102 to an analysis device, such as but not limited to an IMS valve, is closed, and the exhaust valve (e.g., valve 84) is open, permitting the fluid/air to egress the system. During desorption mode, shown in FIG. 5B, sample fluid/air continues to pass through the stack 100 of now-heated analytical preconcentrators 20, desorbing the desired vapors and/or particles. The exhaust valve 84 is closed, and the analysis device valve 102 is open, permitting the fluid/air to enter the analysis device for detection.

Figure 6:
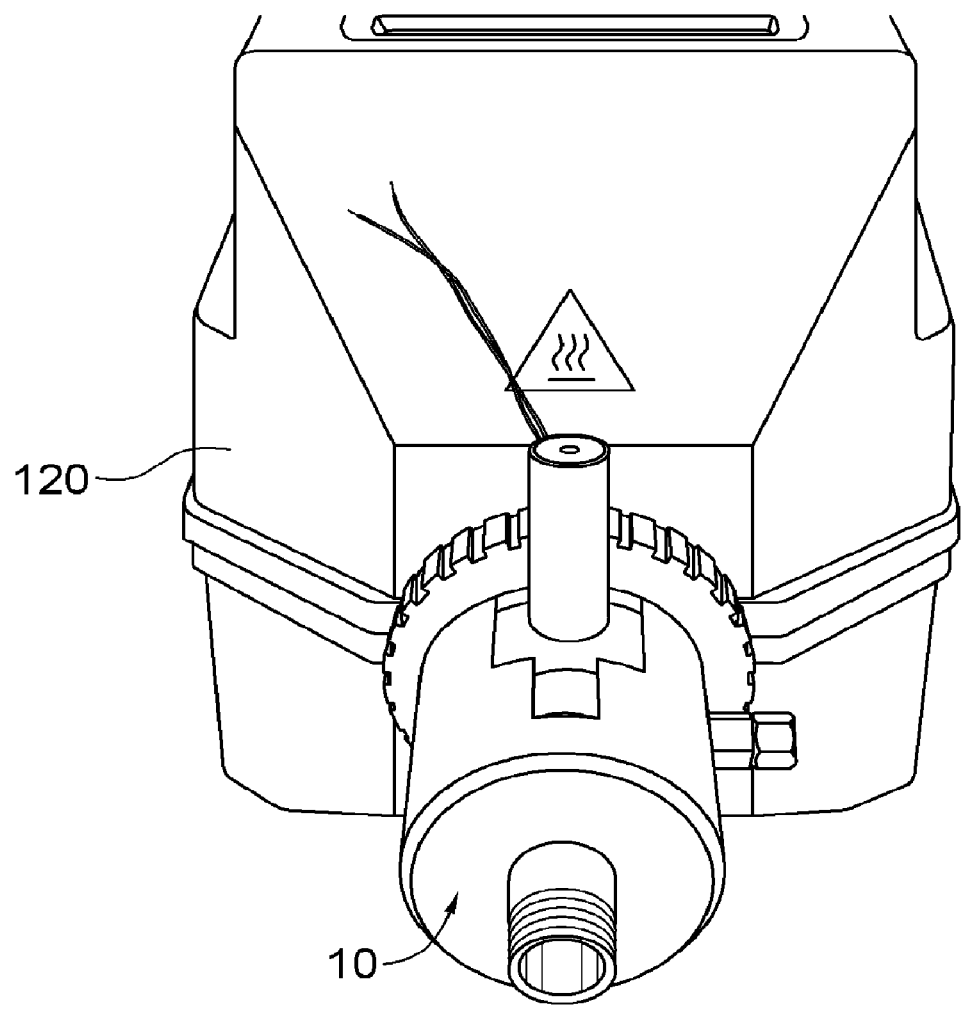
FIG. 6 shows an analysis device attached to the example assembly of FIGS. 1-4.

Referring now to FIG. 6, the complete assembly 10 may be connected to an analysis device 120, such as but not limited to an IMS analysis device, using the threaded ring 74. FIG. 6 shows an experimental embodiment of the FIGS. 1-5 assembly attached to a GE Vapor Trace IMS analysis device. Connecting the assembly 10 to the analysis device 120 in this manner provides a portable collection and analysis device.

Assemblies 10 of the invention provide a number of advantages that will be recognized by artisans in view of the preceding description of the invention. A few examples will be discussed, while artisans will appreciate the more general included use of the inventive assembly 10. The example assembly 10 readily permits stacking, changing, and/or replacement of one or a group of preconcentrator chips 20 to focus analyte particles, e.g., explosive particles at the inlet of an explosive detection system that can be retrofitted to existing detection equipment, including, for example, HVAC systems in a place of high public use (i.e., shopping malls, sporting arenas, amphitheaters, museums, etc.) Another non-limiting example implementation of the assembly 10 provides an interface to stack a group of preconcentrator chips 20 that focus on explosive particles and inherently explosive vapors at the inlet of an explosive detection system that is placed inside a cargo-shipping/in-flight container. A further example of implementation is as an interface to stack a group of preconcentrator chips 20 that focus explosive particles and explosive vapors at the inlet of an explosive detection system that is placed inside waste disposal containers for the detection of potential explosive devices in or on public streets. An additional example implementation is as an implementation to stack a group of preconcentrator chips that focus particles in the slow flow of drinking water to detect heavy metals and/or other harmful compounds. Further example implementations include implementation in explosives, narcotics, chemical, heavy metal, and biological detection systems to increase sensitivity of the detected sample signal.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. An assembly for interchangeably accommodating at least one preconcentrator chip comprising:
    an outer housing and an inner housing defining a chamber;
    a slot in the outer housing permitting insertion of said at least one preconcentrator chip; and
    a biased urging member held at least partially within said outer housing and slidably biased toward a surface of said inner housing;
    wherein when said biased urging member is at least partially retracted, a space is defined between said urging member and the surface of the inner housing for accommodating at least one preconcentrator chip;
    wherein a continuous fluid flow path is defined through said outer housing and through said space, and wherein the fluid flow path is also defined through said biased urging member;
    and wherein said biased urging member comprises a plunger including an at least partially open tube, said plunger including an engaging surface adjacent to said space and an extension that extends at least partially beyond an outer surface of the outer housing, and
    wherein said outer housing comprises a slot for accommodating said extension.

2. An assembly for interchangeably accommodating at least one preconcentrator chip comprising:
    an outer housing and an inner housing defining a chamber;
    a slot in the outer housing permitting insertion of said at least one preconcentrator chip; and
    a biased urging member held at least partially within said outer housing and slidably biased toward a surface of said inner housing;
    wherein when said biased urging member is at least partially retracted, a space is defined between said urging member and the surface of the inner housing for accommodating at least one preconcentrator chip; and
    wherein a continuous fluid flow path is defined through said outer housing and through said space; and
    further comprising at least one modular preconcentrator carriage disposed within the space;
    wherein said at least one preconcentrator carriage is urged by said urging member.

3. The assembly of claim 2, wherein each of said at least one preconcentrator carriage comprises:
    a microscale preconcentrator chip including a plurality of throughholes and a heater for heating a surface of said chip;
    first and second plates at least partially enclosing said chip; and
    at least one electrode coupled to said heater and extending beyond said first and second plates.

4. The assembly of claim 3, wherein each of said at least one preconcentrator carriage further comprises:
    a flex circuit having said at least one electrode provided thereon and coupled to said heater.

5. The assembly of claim 4, wherein said flex circuit comprises a portion extending beyond said first and second plates and having said at least one electrode disposed thereon;
    wherein said outer housing comprises a slot for accommodating the portion of the flex circuit.

6. An assembly for interchangeably accommodating at least one preconcentrator chip comprising:
    housing means for defining a chamber;
    slot means for receiving the at least one preconcentrator chip into said housing means;
    means for accommodating at least one preconcentrator chip disposed within said housing means; and
    means for biasing said at least one preconcentrator chip toward a surface of said housing means;
    means for providing a continuous fluid flow path through said housing means and said means for accommodating;
    at least one preconcentrator chip;
    modular means for enclosing the at least one preconcentrator chip; and
    means for electrically coupling to said at least one preconcentrator chip from outside said modular means for enclosing.

7. The assembly of claim 6, wherein said means for biasing comprises:
- means for urging said modular means toward the surface of said housing means; and
- means for biasing said means for urging.

8. The assembly of claim 7, further comprising:
- means for connecting said housing means to an analysis device such that said chamber is in fluid communication with an inlet of said analytic device.

9. The assembly of claim 8, further comprising:
- means for selectively providing fluid flow out of the chamber independent of the analysis device.

10. An assembly for interchangeably accommodating at least one preconcentrator chip comprising:
- an outer housing and an inner housing defining a chamber;
- a biased urging member held at least partially within said outer housing and slidably biased toward a surface of said inner housing;
- wherein when said biased urging member is at least partially retracted, a space is defined between said urging member and the surface of the inner housing for accommodating at least one preconcentrator chip;
- wherein a continuous fluid flow path is defined through said outer housing and through said space;
- wherein the fluid flow path is also defined through said biased urging member, and said biased urging member comprises a plunger including an at least partially open tube, said plunger including an engaging surface adjacent to said space and an extension that extends at least partially beyond an outer surface of the outer housing; and
- wherein said outer housing comprises a slot for accommodating the extension.

11. An assembly for interchangeably accommodating at least one preconcentrator chip comprising:
- an outer housing and an inner housing defining a chamber;
- a biased urging member held at least partially within said outer housing and slidably biased toward a surface of said inner housing; and
- at least one modular preconcentrator carriage;
- wherein when said biased urging member is at least partially retracted, a space is defined between said urging member and said surface of said inner housing for accommodating at least one preconcentrator chip, and said at least one modular preconcentrator carriage is disposed within said space; and
- wherein said at least one preconcentrator carriage is urged by said urging member; and wherein a continuous fluid flow path is defined through said outer housing and through said space.

12. The assembly of claim 11, wherein each of said at least one preconcentrator carriage comprises;
- a microscale preconcentrator chip including a plurality of throughholes and a heater for heating a surface of said chip;
- first and second plates at least partially enclosing said chip; and
- at least one electrode coupled to said heater and extending beyond said first and second plates.

13. The assembly of claim 12, wherein each of said at least one preconcentrator carriage further comprises:
- a flex circuit having said at least one electrode provided thereon and coupled to said heater.

14. The assembly of claim 13, wherein said flex circuit, comprises a portion extending beyond said first and second plates and having said at least one electrode disposed thereon;
- wherein said outer housing comprises a slot for accommodating the portion of the flex circuit.

15. An assembly for interchangeably accommodating at least one preconcentrator chip comprising:
- housing means for defining a chamber;
- means for accommodating at least one preconcentrator chip disposed within said housing means;
- means for biasing said at least one preconcentrator chip toward a surface of said housing means;
- means for providing a continuous fluid flow path through said housing means and said means for accommodating;
- at least one preconcentrator chip;
- modular means for enclosing the at least one preconcentrator chip; and
- means for electrically coupling to said at least one preconcentrator chip from outside said modular means for enclosing.

16. The assembly of claim 15, wherein said means for biasing comprises:
- means for urging said modular means toward the surface of said housing means; and
- means for biasing said means for urging.

17. The assembly of claim 16, further comprising:
- means for connecting said housing means to an analysis device such that the chamber is in fluid communication with an inlet of the analysis device.

18. The assembly of claim 17, further comprising:
- means for selectively providing fluid flow out of the chamber independent of the analysis device.

19. An interchangeable preconcentrator connector assembly that permits rapid sequential insertion and removal of packaged analytical microscale preconcentrators into a stacked formation to focus or preconcentrate a desired sample of vapors and/or particles prior to desorption into a storage or analysis instrument, the assembly comprising:
- inner and outer housings configured to connect to an analysis instrument, define fluid flow paths, and space for accommodating other parts of the assembly, including a space for one or plurality of microscale preconcentrators held in a protective carriage that includes electrodes for connection to a control circuit;
- a biased member in the assembly slidably held in said outer housing and biased to push against inserted preconcentrator(s) carriages to align and secure them such that fluid flow will be primarily through the preconcentrators from an inlet to the assembly defined by a fluid flow path in said biased member; and
- valves in the assembly to enable flows for preconcentration that are independent from flows of the analysis instrument,
- wherein at least partial retraction of said biased member permits said at least one preconcentrator to be inserted into and removed from said outer housing;
- wherein said biased member further comprises a plunger including an at least partially open tube, said plunger including an engaging surface adjacent to said space, said plunger includes an extension that extends at least partially beyond an outer surface of the outer housing, and said outer housing comprises a slot for accommodating said extension.

* * * * *